(12) United States Patent
Rukmini Jayaraman et al.

(10) Patent No.: US 10,358,640 B2
(45) Date of Patent: Jul. 23, 2019

(54) PROCESS FOR SEPARATION OF PROKARYOTIC DNA FROM EUKARYOTIC DNA IN A WHOLE BLOOD SAMPLE

(71) Applicant: SIEMENS HEALTHCARE GMBH, Erlangen (DE)

(72) Inventors: Subhadra Rukmini Jayaraman, Karnataka (IN); Ramya Vutukuru, Karnataka (IN)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 104 days.

(21) Appl. No.: 15/508,202

(22) PCT Filed: Aug. 18, 2015

(86) PCT No.: PCT/EP2015/068936
§ 371 (c)(1),
(2) Date: Mar. 2, 2017

(87) PCT Pub. No.: WO2016/034405
PCT Pub. Date: Mar. 10, 2016

(65) Prior Publication Data
US 2019/0085316 A1  Mar. 21, 2019

(30) Foreign Application Priority Data
Sep. 3, 2014  (IN) .............................. 909/KOL/2014

(51) Int. Cl.
*C12N 15/10* (2006.01)
*C12Q 1/6806* (2018.01)
(52) U.S. Cl.
CPC ....... *C12N 15/1006* (2013.01); *C12Q 1/6806* (2013.01)

(58) Field of Classification Search
None
See application file for complete search history.

(56) References Cited

U.S. PATENT DOCUMENTS

| 8,481,262 B2 | 7/2013 | Schmidt et al. |
| 2013/0017552 A1 | 1/2013 | Rudorfer |
| 2014/0127687 A1 | 5/2014 | Osterloh et al. |

OTHER PUBLICATIONS

Horz (Journal of Microbiological Methods 72 (2008) 98-102).*
PCT International Search Report and Written Opinion of the International Searching Authority dated Oct. 13, 2015 for corresponding PCT/EP2015/068936.

* cited by examiner

*Primary Examiner* — Amanda Haney
(74) *Attorney, Agent, or Firm* — Lempia Summerfield Katz LLC

(57) ABSTRACT

A process for separating prokaryotic DNA from eukaryotic DNA in a whole blood sample infected by pathogen is provided. The process includes extracting prokaryotic and eukaryotic DNA from the whole blood sample, contacting the prokaryotic DNA in the whole blood sample with a motif that specifically binds to the prokaryotic DNA, and generating a bound pair. The process also includes separating the bound pair. The whole blood sample is transfected with bacteriophages genetically modified to contain a defined DNA sequence having a selectable marker DNA. The DNA sequence integrates into the prokaryotic DNA, and the motif is an oligonucleotide specific to the defined DNA sequence in the engineered bacteriophages.

9 Claims, 2 Drawing Sheets

PROCESS FOR SEPARATION OF PROKARYOTIC DNA FROM EUKARYOTIC DNA IN A WHOLE BLOOD SAMPLE

CROSS-REFERENCE TO RELATED APPLICATIONS

This application is the National Stage of International Application No. PCT/EP2015/068936, filed Aug. 18, 2015, which claims the benefit of Indian Patent Application No. 909/KOL/2014, filed Sep. 3, 2014. The entire contents of these documents are hereby incorporated herein by reference

BACKGROUND

The present embodiments relate to a process for separating prokaryotic DNA from eukaryotic DNA in a given whole blood sample infected by pathogen.

Separating prokaryotic DNA from eukaryotic DNA may be performed by contacting at least one prokaryotic DNA with a protein that is specific to the prokaryotic DNA, thus forming a protein-DNA complex. The protein is 25% to 35% homologous to wild type CGPB protein. Such protein binds to non-methylated CpG motifs in the prokaryotic DNA. Such protein-DNA complex is separated, and the prokaryotic DNA is further separated from the protein-DNA complex. The process is based on the principle that prokaryotic DNA is non-methylated; thus, a protein specific to non-methylated CpG motifs in the prokaryotic DNA is used to separate the prokaryotic DNA. This process may not be specific to prokaryotic DNA, as eukaryotic DNA may be non-methylated under conditions like cancer and old age. Under such conditions, certain motifs of the eukaryotic DNA may be non-methylated and may get separated along with the prokaryotic DNA in the given sample.

SUMMARY AND DESCRIPTION

The scope of the present invention is defined solely by the appended claims and is not affected to any degree by the statements within this summary.

One or more of the present embodiments may obviate one or more of the drawbacks or limitations in the related art. For example, a process that is more efficient and specific in separation of prokaryotic DNA from eukaryotic DNA, allowing for higher recovery of the required prokaryotic DNA during the separation process, is provided.

One or more of the present embodiments provides that the whole blood sample is transfected with bacteriophages genetically modified to contain a defined DNA sequence having a selectable marker DNA. The DNA sequence integrates into the prokaryotic DNA, and the motif is an oligonucleotide complementary to the defined DNA sequence in the engineered bacteriophages.

One or more of the present embodiments provide for a process that is more efficient and specific, providing a higher recovery of prokaryotic DNA as compared to currently known methods. A process for separating prokaryotic DNA from eukaryotic DNA in a whole blood sample is provided. A whole blood sample is collected from a patient to be tested using a needle, and the DNA from the whole blood sample infected by pathogen is extracted such that the prokaryotic DNA is also extracted along with the eukaryotic DNA. A whole blood sample refers to blood drawn from human body from which no constituents (e.g., platelets or plasma) have been removed. A prokaryotic DNA refers to the DNA of a single cellular organism that does not have a membrane bound nucleus. A eukaryotic DNA refers to the DNA of an organism with cells having a nucleus and other organelles bound within membranes. Extracting DNA provides easier detection and separation of pathogenic prokaryotic DNA from the given whole blood sample.

The extracted prokaryotic DNA is brought in contact with a motif that specifically binds to the prokaryotic DNA. A motif refers to a sequence pattern of nucleotides in a DNA sequence. Once the prokaryotic DNA binds to the motif, a bound pair is generated. The bound pair is separated for further analysis.

The whole blood sample is transfected with bacteriophages that have been genetically modified to contain a defined DNA sequence containing a selectable marker DNA. The DNA sequence integrates into the prokaryotic DNA. Transfection is a process by which a virus or a bacteriophage introduces a DNA or RNA molecule into bacterial cells resulting in infection. A selectable marker DNA is a DNA sequence used in molecular biology to provide that a particular DNA sequence has been inserted into an organism's DNA.

The motif used for separating the prokaryotic DNA is an oligonucleotide specific to the defined DNA sequence in the engineered bacteriophages. The complex formed between the oligonucleotide and the defined DNA sequence helps in isolating the prokaryotic DNA in which the defined DNA sequence has been integrated from eukaryotic DNA.

According to one or more of the present embodiments, the whole blood sample is transfected with the engineered bacteriophages before genomic DNA is extracted from the whole blood sample. Thus, when the eukaryotic DNA and the prokaryotic DNA is extracted, the defined DNA sequence has already been integrated into the prokaryotic DNA. This act allows detection and separation of the prokaryotic DNA to be performed more easily and more efficiently.

According to one or more of the present embodiments, the pathogen to be detected in the whole blood sample is a bacterium (e.g., bacteriophages transfect bacteria).

According to one or more of the present embodiments, the prokaryotic DNA is bacterial DNA.

According to one or more of the present embodiments, the bacteriophage is engineered and used for transfection of the pathogenic bacteria is a lysogenic bacteriophage. A bacteriophage undergoing lytic cycle of reproduction on transfection would degrade the bacterial DNA. In order to keep the bacterial DNA intact and the phage genome integrating into such bacterial DNA, a bacteriophage employing lysogenic cycle of reproduction is chosen.

According to one or more of the present embodiments, the oligonucleotide is bound to a carrier. The binding of the oligonucleotide to a carrier facilitates immobilization. The carrier is an adsorbent micro particle, a membrane, or a matrix, and allows the oligonucleotide to bind to a surface of the oligonucleotide.

According to one or more of the present embodiments, the prokaryotic DNA is separated from the oligonucleotide of the bound pair after separating the bound pair. Separating the bound pair provides that the prokaryotic DNA is made available in a pure form for further experiments. Separating the prokaryotic DNA from oligonucleotide of the bound pair may be performed by an elution buffer. Elution buffer is a solvent that, at higher concentrations, releases the desired motif from the ligand.

According to one or more of the present embodiments, the eukaryotic DNA is human genomic DNA.

DETAILED DESCRIPTION

Figure 1:
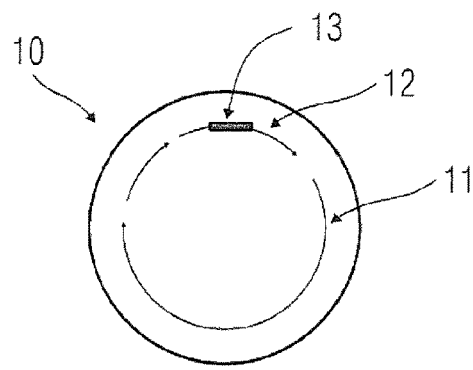
FIG. 1 illustrates a schematic diagram of a genome of an engineered bacteriophage containing defined DNA sequence and a selectable marker DNA.

Hereinafter, one or more of the present embodiments are described in detail. The various embodiments are described with reference to the drawings, where like reference numerals are used to refer to like elements throughout. In the following description, for purpose of explanation, numerous specific details are set forth to provide a thorough understanding of one or more of the present embodiments. Such embodiments may be practiced without these specific details.

FIG. 1 illustrates the genomic DNA of an engineered bacteriophage 10. In the embodiment shown in FIG. 1, the bacteriophage 10, employing a lysogenic cycle of reproduction, is chosen and is genetically engineered. A lysogenic cycle of reproduction is one way of reproduction, where the nucleic acid of the bacteriophage 10 is integrated into the genome of the bacterium the bacteriophage 10 infects. The viral genome propagates along with the bacterial DNA when the bacterium undergoes genetic division. In the lysogenic phase, the bacterial cells are not lysed contrarily to lytic cycle of viral reproduction. The lysogenic bacteriophage may be chosen such that the lysogenic bacteriophage is capable of transfecting different types of pathogenic bacteria infecting the whole blood sample (e.g., M13 phage delivery system). However, a concoction of multiple bacteriophages for transfecting the pathogens that may be present in the given whole blood sample may be used. In an embodiment, genomic DNA of bacteriophage 10 may be modified to include a defined DNA sequence 12 integrated within bacteriophage genomic DNA 11. The defined DNA sequence 12 to be introduced into the bacteriophage 19 includes a balanced nucleobase content and a selectable marker DNA 13. In an embodiment, the selectable marker DNA 13 may be an antibiotic resistance gene. A selectable marker DNA is a nucleotide sequence that helps in successfully introducing foreign DNA into a cell. The antibiotic resistance gene helps in choosing bacterial cells that have the defined DNA sequence in their genomic DNA.

Figure 2:
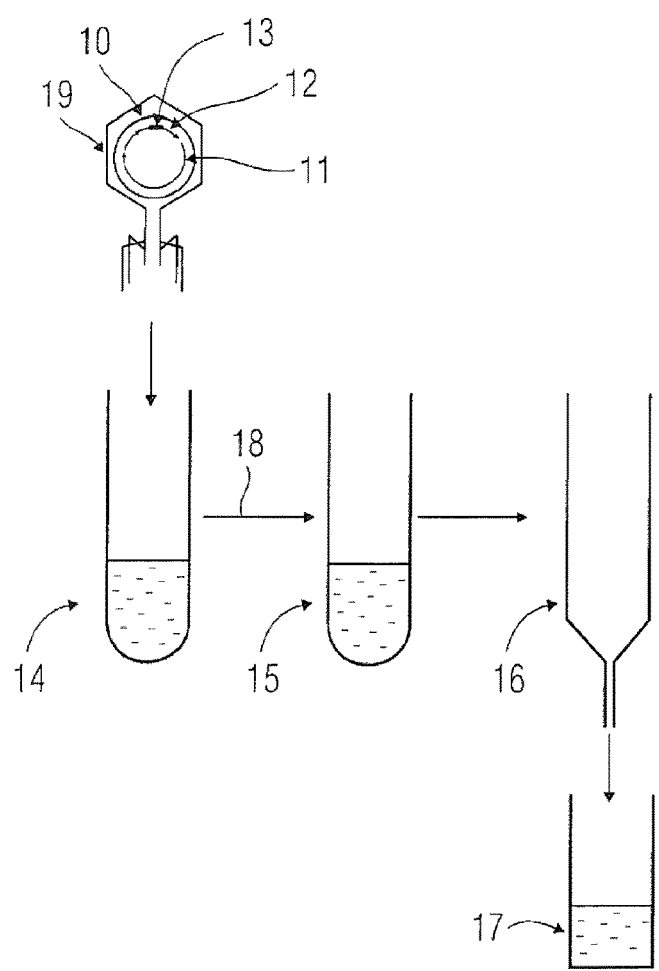
FIG. 2 illustrates a schematic diagram of an embodiment of a process for separating prokaryotic DNA from eukaryotic DNA from a whole blood sample infected by pathogen.

FIG. 2 illustrates an embodiment of a process for separating prokaryotic DNA from eukaryotic DNA in a whole blood sample infected by pathogen. In the embodiment shown in FIG. 2, the genetically modified lysogenic bacteriophage 19 is added to the whole blood sample 14 collected from a patient. Whole blood refers to blood drawn from human body from which no constituents (e.g., platelets or plasma) have been removed. The engineered bacteriophages 19 (e.g., in the range of $10^6$ and $10^9$ PFU in approximately 200 µL saline) are inoculated in the whole blood sample 14. The engineered bacteriophages 19 transfect pathogenic bacteria present in the whole blood sample 14 and start the lysogenic cycle. Thus the engineered genome 10 integrates into the bacterial genome. The bacterial genome is the prokaryotic DNA of interest that is separated. Transfection is a process in which a prokaryotic virus or a bacteriophage infects a bacterium and transfers the viral DNA into the bacterium.

In act 18, genomic DNA is extracted from the whole blood sample 14 such that the prokaryotic DNA from the pathogenic bacteria is also released. The extraction methods used are well known to persons skilled in the art. A lysing mixture is added to the whole blood sample 14, for extracting the genomic DNA, releasing the internal cellular components of the pathogenic bacteria. The lysing mixture also breaks down the blood cells in the sample and releases a substantial amount of eukaryotic DNA.

The prokaryotic DNA is then separated from the eukaryotic DNA released in the extraction process. In an embodiment, an oligonucleotide (e.g., specific to the defined DNA sequence integrated within the prokaryotic DNA) bound to a carrier molecule is used for separating the prokaryotic DNA from the whole blood sample 14. The carrier molecule is an adsorbent and may be a micro-particle, a membrane, or a matrix, so as to facilitate binding of the oligonucleotide on a surface of the oligonucleotide. The oligonucleotide binds to the prokaryotic DNA and forms a bound pair complex. Such a bound pair complex helps in separating 16 the prokaryotic DNA from eukaryotic DNA and other cellular components released in the blood sample. The prokaryotic DNA is then separated 17 from the oligonucleotide of the bound pair complex.

Various methods may be employed to separate 16 the bound pair complex of the prokaryotic DNA and the oligonucleotide. Such methods are explained in detail as non-limiting examples.

Example 1: Separation by Affinity Chromatography

In an embodiment, an affinity chromatography method may be used for separating the prokaryotic DNA. In the embodiment, carrier molecules bound to the oligonucleotides having affinity towards the prokaryotic DNA are introduced in a column 16. The lysed mixture 15 containing extracted genomic DNA and prokaryotic DNA is passed through the column, and the flow through obtained is collected. The collected flow through is passed through a second column containing carrier molecules bound to the oligonucleotides. The prokaryotic DNA of interest in the whole blood sample binds to the oligonucleotides in the columns, allowing eukaryotic DNA and other cellular components to flow through the columns. The columns are washed with a wash buffer to remove any unspecific DNA or debris bound to the columns. An elution buffer may be used to release 17 the bound prokaryotic DNA from the oligonucleotide. The buffer releases the prokaryotic DNA from the carrier by binding to the carrier in place of the prokaryotic DNA.

Example 2: Separation by Lateral Flow Assay

Lateral flow assay is a method that helps in detection and separation of an analyte of interest from given sample. In an embodiment, the lysed whole blood sample 15 containing eukaryotic DNA and prokaryotic DNA is added on a lateral flow strip 16 including a conjugate pad, a nitrocellulose membrane, and an absorbent pad. The conjugate pad contains gold nano-particle probes having complementary sequences to the defined DNA sequence 12 integrated into the prokaryotic DNA. The nitrocellulose membrane contains two zones, detection zone and control zone. The detection zone contains the oligonucleotides complementary to the prokaryotic DNA and the control zone contains an oligonucleotide sequence specific to gold nano-particle probe. The absorbent pad absorbs the excess of the sample.

When the lysed blood sample 15 is added on the lateral flow strip, the prokaryotic DNA binds with the gold nano-particle probe and flows down the strip. A complex formed between the prokaryotic DNA and gold nano-particle probe binds to the oligonucleotide present in the detection zone of the nitrocellulose membrane. The unbound gold nano-particles flow down and bind to the control zone of the nitrocellulose membrane. The prokaryotic DNA bound to gold nano-particle probe and oligonucleotide in the detection zone may be eluted 17 using an elution buffer.

Example 3: Biotin Based Magnetic Separation

Biotin is an affinity molecule that is widely used for detection and separation of biological molecules. Biotin has a very strong affinity for streptavidin protein, and thus, may be used for separating analytes of interest. In an embodiment, the oligonucleotide sequence complementary to the prokaryotic DNA to be separated is labeled with biotin. Once the lysed whole blood sample 15 is treated with the biotinylated oligonucleotide, the prokaryotic DNA in the whole blood sample 14 binds to such oligonucleotide and forms a complex. In the embodiment, the whole blood sample with the complex is exposed to streptavidin molecules bound to magnetic beads. In the presence of streptavidin molecule, biotinylated oligonucleotide and the prokaryotic DNA binds to the streptavidin molecule. Such a complex formed may be separated by application of a magnetic field. Thus, the prokaryotic DNA may be separated from the eukaryotic DNA and other cellular components.

Figure 3:
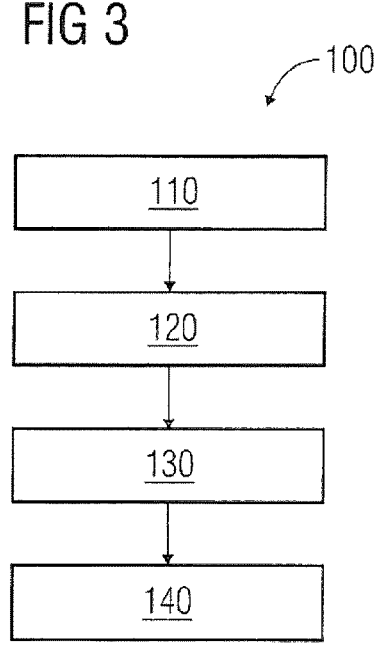
FIG. 3 illustrates a flowchart of an embodiment of a method for separating prokaryotic DNA from eukaryotic DNA in a whole blood sample.

FIG. 3 is a flowchart illustrating an embodiment of a process for separating prokaryotic DNA from eukaryotic DNA from a whole blood sample infected by pathogen. The process 100 includes the following acts. At act 110, genetically engineered bacteriophages 19 are added to the whole blood sample 14 to allow the engineered bacteriophages 19 to infect the bacteria in the whole blood sample 14. At act 120, eukaryotic and prokaryotic DNA from the whole blood sample 14 is extracted. At act 130, the prokaryotic DNA in the lysed whole blood sample 15 is separated 16 from the eukaryotic DNA by adding the lysed whole blood sample 15 to carrier molecules bound to oligonucleotides specific to the defined DNA sequence 12 integrated into the prokaryotic DNA. The defined DNA sequence 12 binds to the oligonucleotides on the carrier molecules and form a bound pair complex. At act 140, the bound pair complex is eluted out 17 using an elution buffer.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

We claim:

1. A process for separation of prokaryotic DNA from eukaryotic DNA in a given whole blood sample infected by pathogen, the process comprising:
   extracting the prokaryotic DNA and the eukaryotic DNA from the whole blood sample;
   contacting the prokaryotic DNA in the whole blood sample with a motif that specifically binds to the prokaryotic DNA and generates a bound pair; and
   separating the bound pair,
   wherein the whole blood sample is transfected with bacteriophages genetically modified to contain a defined DNA sequence having a selectable marker DNA,
   wherein the defined DNA sequence integrates into the prokaryotic DNA, and
   wherein the motif is an oligonucleotide specific to the defined DNA sequence in the bacteriophages.

2. The process of claim 1, wherein the pathogen is a bacterium.

3. The process of claim 1, wherein the prokaryotic DNA is bacterial DNA.

4. The process of claim 1, wherein the bacteriophages are lysogenic bacteriophages.

5. The process of claim 1, wherein the oligonucleotide is bound to a carrier.

6. The process of claim 5, wherein the carrier is an adsorbent micro-particle, a membrane, or a matrix.

7. The process of claim 1, wherein the separating of the bound pair is followed by separating the prokaryotic DNA from the oligonucleotide of the bound pair.

8. The process of claim 7, wherein the separation of prokaryotic DNA from the oligonucleotide is performed by an elution buffer.

9. The process of claim 1, wherein the eukaryotic DNA is human genomic DNA.

* * * * *